United States Patent
Uda (10) Patent No.: US 10,893,990 B1
(45) Date of Patent: Jan. 19, 2021

(54) METHOD AND APPARATUS FOR TREATING AN INSIDE VOLUME OF A MOBILE VEHICLE

(71) Applicant: PetAirapy, LLC, St. Charles, IL (US)

(72) Inventor: Mike M. Uda, St. Charles, IL (US)

(73) Assignee: PetAirapy, LLC, St. Charles, IL (US)

( * ) Notice: Subject to any disclaimer, the term of this patent is extended or adjusted under 35 U.S.C. 154(b) by 0 days.

(21) Appl. No.: 16/852,277

(22) Filed: Apr. 17, 2020

Related U.S. Application Data (63) Continuation-in-part of application No. 16/844,815, filed on Apr. 9, 2020.

(51) Int. Cl.
*A61G 3/00* (2006.01)
*B60H 3/00* (2006.01)
*A61L 9/20* (2006.01)

(52) U.S. Cl.
CPC ........... *A61G 3/008* (2013.01); *B60H 3/0085* (2013.01); *A61L 9/20* (2013.01)

(58) Field of Classification Search
CPC .......... A61G 3/008; B60H 3/0085; A61L 9/20
See application file for complete search history.

(56) References Cited

U.S. PATENT DOCUMENTS

| | | | |
|---|---|---|---|
| 6,908,597 B2 * | 6/2005 | Chen | A61L 9/20 422/1 |
| 10,363,329 B2 * | 7/2019 | Childress | H05B 47/16 |
| 2015/0086420 A1 * | 3/2015 | Trapani | A61L 9/015 422/24 |
| 2016/0271289 A1 * | 9/2016 | Duffy | A61L 9/20 |
| 2019/0091738 A1 * | 3/2019 | Chen | B08B 7/0057 |
| 2020/0254125 A1 * | 8/2020 | Lloyd | A61L 2/10 |

FOREIGN PATENT DOCUMENTS

| | | | | |
|---|---|---|---|---|
| KR | 20150017544 A | * | 2/2015 | B60H 3/00 |

OTHER PUBLICATIONS

Translation of Won (Year: 2015).*
International Ultraviolet Association (Year: 0).*
Petairapy, "Mobile Service System Solution PAD-N06", 2018, Saint Charles, IL.

* cited by examiner

*Primary Examiner* — Sean E Conley
*Assistant Examiner* — Brendan A Hensel
(74) *Attorney, Agent, or Firm* — Wood, Phillips, Katz, Clark & Mortimer (57) ABSTRACT

A treatment apparatus and method of treating an inside volume of a mobile vehicle using the apparatus. The method includes the steps of: a) placing a treatment unit in an operative position with respect to the mobile vehicle, the treatment unit having: i) a frame; ii) a source of UV light; and iii) an air mover for controllably directing air within the inside volume to be exposed to UV rays generated by the UV light source; and b) operating the treatment unit and thereby causing air within the inside volume to be disinfected by UV light rays from the UV light source and circulated within the inside volume.

19 Claims, 3 Drawing Sheets

“Mobile Service System Solution PAD-
METHOD AND APPARATUS FOR TREATING AN INSIDE VOLUME OF A MOBILE VEHICLE

CROSS-REFERENCE TO RELATED APPLICATIONS

This application is a continuation-in-part of U.S. patent application Ser. No. 16/844,815 filed Apr. 9, 2020.

BACKGROUND OF THE INVENTION

Field of the Invention

This invention relates to environmental air and surface treatment and, more particularly, to a treatment unit that disinfects using UV light rays and a method of using such a treatment unit within an internal volume of a mobile vehicle.

Background Art

UV-C, also known as "germicidal ultraviolet" light, is known to deactivate molds, spores, germs, viruses, bacteria, allergens, and other pollutants that contaminate environmental air and hard surfaces. Infectious pathogens may remain active for lengthy periods. Consequently, air and surface transmission have serious consequences to humans and animals alike, which raises the risk of an outbreak. The recent coronavirus pandemic has highlighted the need worldwide to take more precautionary steps to limit dangerous microorganism exposure on a routine basis, with particular focus on those whose professions routinely place them at a higher risk of exposure to dangerous microorganisms that can have severe health consequences—most notably those in the emergency response category.

Generally, at the top of the list of those in this high risk category are those in the mobile medical industry. There is also a recognition that those not always directly involved in supervising and handling medical situations, such as policemen, firemen, etc., regularly place themselves in this high risk category by regularly contacting, and being in close proximity to, persons that may be dangerous microorganism transmitters.

While not in the emergency response category, veterinarians utilizing mobile vehicles to transport animals are also at high risk of contracting disease through animal transmission of microorganisms. In the animal care industry, mobile vehicles are used for many different purposes, including transporting pets for adoption, making house calls, rescue calls, and grooming calls, etc. Commonly, mobile vehicles will have a relatively small occupancy space for both workers and the animals that they tend to. As a result, workers will be in close proximity to the animals, which creates a risk of potentially harmful microorganism transmission. A single mobile vehicle may admit dozens of different animals over a relatively short time period which, aside from creating the dangers associated with instant contact, progressively may build up dangerous microorganisms on surfaces throughout the vehicle which may survive for hours or days.

The coronavirus has appropriately shifted attention to the dangers faced by emergency responders in mobile vehicles. For example, a single ambulance will pick up many different patients and will transport a large number of different personnel who are in turn exposed to many potentially contaminated surfaces and human germ transmitters. These persons will occupy a relatively small internal volume within the vehicle and contact surfaces throughout the internal volume thereof. These contact surfaces are, for example, on treatment devices, electronic components with touch controls and manipulating surfaces, etc.

Men and women police personnel also routinely transport different persons within the same contiguous volume that they reside. These persons may be sick or may carry diseases which then places the law enforcement personnel at continuing and high risk. As with an ambulance setting, internal volumes within mobile police vehicles will commonly be visited by many different persons from the public and other law enforcement personnel who share a small air volume and repetitively touch equipment and other internal surfaces. Each such person represents a potential direct or indirect transmitter of dangerous microorganisms.

The same risks exist in mobile firefighting vehicles and virtually every mobile public service vehicle that is required to visit different locations, share close air space with different individuals, and touch surfaces that are touched by many known and unknown individuals.

Many public service vehicles include, within the internal volume occupied by the operating personnel, specialized equipment that may be made up of potentially a large number of components that are placed throughout the volume and which may have to be contacted to perform operations therewith. Thus, there are a multitude of surfaces that are repetitively contacted by different personnel acting in different shifts and by many public persons that are encountered on the street without any ability to predetermine whether or not they have infectious conditions.

The inventor herein has developed commercially available systems for treating surfaces in mobile vehicles with UV light to effect sanitation thereof. One such system is identified as the "Mobile Service System Solution PAD-N06." This system has been designed principally for mobile vehicles having equipment such as counters, tables, cages, crates, and other medical equipment required for different tasks associated with the animal care industry. Since exposure to UV light rays can be dangerous to human beings and animals, the system is designed to treat an internal volume only when the internal volume is unoccupied by any human or animal. Certain safeguards have been devised so that the system will not operate with an occupant present.

While the above system has been effective, it has one limitation in that the sanitation exercise must be interrupted while the mobile vehicle is occupied. Thus, even if prior to occupation by a driver or passenger effective disinfecting is carried out, an ongoing risk of new contamination or recontamination arises as potentially different microorganisms find their way back into the internal volume through environmental air, persons, or animals. This problem is aggravated by the fact that often these types of vehicles may be handed off from one worker or shift to the next, whereby there is extended, uninterrupted use which does not permit sanitation using the above-described system.

Thus, personnel operating in such vehicles, particularly when there is a high risk situation, such as a pandemic, face an ongoing risk of infection. Every human is a potential virus carrier. The problem is aggravated by the fact that many carriers are asymptomatic, whereby there is no perceivable sign that they pose a risk of transmission.

Scientists in the health field have become increasingly aware of the need to protect those in public service from dangerous germs, and particularly those in the emergency responder category. The industry has an interest not only in protecting those currently employed, but attracting future talent that will not be discouraged from entering the field because of perceived health risks. The industry continues to seek out reasonable measures to reduce the likelihood of exposure of personnel operating mobile vehicles, particularly in emergency response situations, to dangerous microorganisms that are airborne or survive on regularly contacted surfaces.

SUMMARY OF THE INVENTION

In one form, the invention is directed to a method of treating an inside volume of a mobile vehicle. The method includes the steps of: placing a treatment unit in an operative position with respect to the mobile vehicle; and operating the treatment unit. The treatment unit has: a frame; a source of UV light; and an air mover for controllably directing air within the inside volume to be exposed to UV rays generated by the UV light source. Operating the treatment unit causes air within the inside volume to be disinfected by UV light rays from the UV light source and circulated within the inside volume.

In one form, the air mover consists of at least one fan.

In one form, the step of placing the treatment unit in the operative position involves mounting the frame to a ceiling on the mobile vehicle.

In one form, the mobile vehicle has at least one seat for an occupant. The method further includes the step of operating the treatment unit with a person situated in the at least one seat.

In one form, the mobile vehicle has a driver's seat. The method further includes the step of operating the treatment unit with a person situated in the driver's seat.

In one form, the method further includes the step of operating the treatment unit with the person in the driver's seat operating the mobile vehicle.

In one form, the treatment unit is changeable between: a) a first state wherein a predetermined part of the inside volume is strategically blocked from direct exposure to UV light rays generated by the UV light source; and b) a second state wherein at least a portion of the predetermined part of the inside volume is directly exposed to UV light rays from the UV light source. The step of operating the treatment unit with a person situated in the at least one seat is performed with the treatment unit in the first state so that the person situated in the at least one seat is not directly exposed to UV light rays from the UV light source.

In one form, the method further includes the step of changing the treatment unit into the second state and operating the treatment unit in the second state without any person situated in the inside volume.

In one form, the treatment unit has on and off states and a delayed start timer. The method further includes the step of activating the delayed start timer to allow a person actuating the delayed start timer from within the inside volume to exit the inside volume before the treatment unit is changed from the off state into the on state with the treatment unit in the second state.

In one form, the treatment unit has at least one blocking part. The method further includes the step of changing the treatment unit between the first and second states by repositioning the at least one blocking part.

In one form, the invention is directed to a method of treating an inside volume of a mobile vehicle as described above wherein the mobile vehicle has: a) a dashboard; b) a steering wheel; c) seat surfaces against which at least one occupant can bear to be maintained in a sitting position; and d) a peripheral wall surface bounding the inside volume. With the treatment unit in the second state, operating the treatment unit causes UV light rays generated by the UV light source to be directed against at least part of at least one of: i) the dashboard; ii) the steering wheel; iii) the seat surfaces; and iv) the peripheral wall surface.

In one form, with the treatment unit in the second state, operation of the treatment unit causes UV light rays generated by the UV light source to be directed against at least part of each of: a) the dashboard; b) the steering wheel; c) the seat surface; and d) the peripheral wall surface.

In one form, the mobile vehicle is an emergency vehicle with electronic emergency equipment with operating components exposed within the inside volume.

In one form, the UV light source has at least one elongate bulb with a length. The step of operating the treatment unit involves causing the air mover to move air in a flow path lengthwise of the at least one elongate bulb.

In one form, the method further includes the step of changing the treatment unit between the first and second states by manually repositioning a part of the treatment unit.

In one form, the treatment unit has an actuator. The method further includes the step of causing the actuator to reposition a part of the treatment unit to thereby change the treatment unit between the first and second states.

In one form, the method further includes the step of controlling the actuator from a location spaced from the actuator.

In one form, the air mover is mounted on the frame.

In one form, the mobile vehicle has an entry door that has open and closed positions. The treatment unit has on and off states and a disabling structure. The method further includes the step of causing the disabling structure to change the treatment unit in the on and second states to be changed into the off state as an incident of the entry door changing from the closed position into the open position.

In one form, the UV rays generated by the UV light source are not capable of penetrating glass.

In one form, the invention is directed to the treatment unit as described above.

In one form, the treatment unit is provided in combination with the mobile vehicle described above, with respect to which the treatment unit is placed in the operative position.

In one form, the air mover consists of at least one fan.

In one form, the mobile vehicle has a ceiling. The treatment unit in the operative position is on the ceiling of the movable vehicle.

In one form, the treatment unit is changeable between: a) a first state wherein a predetermined part of the inside volume is strategically blocked from direct exposure to UV light rays generated by the UV light source; and b) a second state wherein at least a portion of the predetermined part of the inside volume is directly exposed to UV light rays from the UV light source.

In one form, the treatment unit has on and off states. The treatment unit has a delayed start timer which can be set to cause the treatment unit to change from the off state into the on state after a predetermined time interval.

In one form, the treatment unit has at least one blocking part that is repositionable to change the treatment unit between the first and second states.

In one form, the mobile vehicle has: a) a dashboard; b) a steering wheel; c) seat surfaces against which at least one occupant can bear to be maintained in a sitting position; and d) a peripheral wall surface bounding an inside volume. All of a)-d) have UV light rays generated by the UV light source directed thereagainst with the treatment unit in the second state.

In one form, the mobile vehicle is an emergency vehicle with electronic emergency equipment with operating components exposed within the inside volume.

In one form, the mobile unit has an entry door that has open and closed positions. The treatment unit has a disabling feature that causes the treatment unit to be changed from the second state into the first state as an incident of the door being changed from the closed position into the open position.

DETAILED DESCRIPTION OF THE PREFERRED EMBODIMENT

Figure 1:
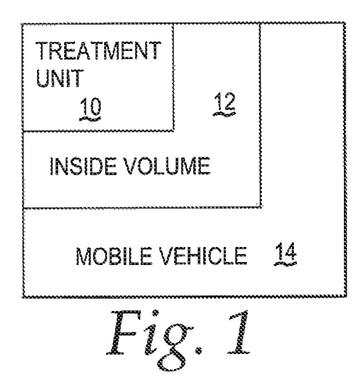
FIG. 1 is a schematic representation of a mobile vehicle with a treatment unit, according to the present invention, in an operative position thereon.

As depicted schematically in FIG. 1, the invention is directed to a treatment unit 10 that disinfects an inside volume 12 of a mobile vehicle 14, with the capability of continuing to treat the inside volume 12 safely even when occupied by a human or animal.

Figure 2:
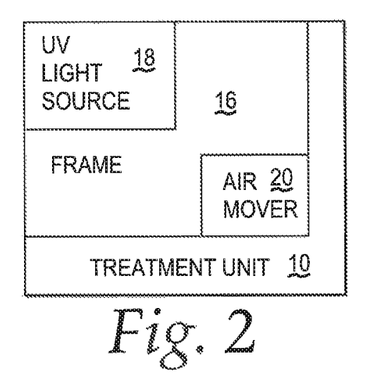
FIGS. 2 and 3 show different variations of the treatment unit as shown generically in FIG. 1.

As shown in FIG. 2, the treatment unit 10 has a frame 16 with an associated UV light source 18 that generates germicidal ultraviolet light rays. The use of this type of light source for disinfecting purposes is described more fully in U.S. patent application Ser. No. 15/871,719, filed on Jan. 15, 2018, the disclosure of which is incorporated herein by reference.

An air mover 20 is provided on the frame 16 to controllably direct air within the inside volume 12 so as to be exposed to UV rays generated by the UV light source 18.

Figure 3:
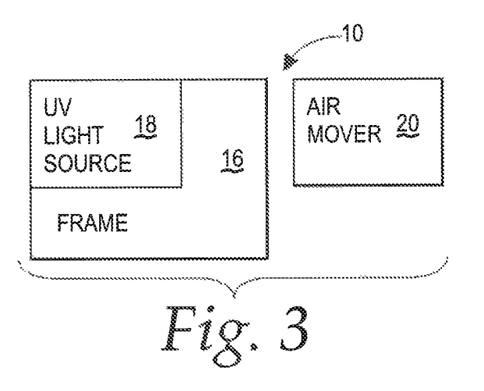

In an alternative form as shown in FIG. 3, a treatment unit 10, with the aforementioned frame 16 and UV light source 18, may have an air mover 20 that is associated with but not directly provided upon the frame 16.

In either form, it is anticipated that the air mover 20 is dedicated to the function of the treatment unit 10 as opposed to relying solely upon air movement effected through conventional heating and air conditioning systems that are provided as original equipment on user occupiable mobile vehicles.

Figure 4:
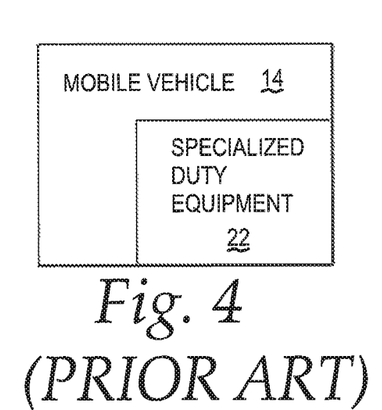
FIG. 4 is a schematic representation of a conventional mobile vehicle of a type to which the inventive treatment unit can be adapted.

While the mobile vehicle 14 could be any type of drivable vehicle, as shown in FIG. 4, the mobile vehicle 14 focused upon herein is one with equipment dedicated to a function beyond simply passenger and basic cargo transportation. As indicated schematically in FIG. 4, the mobile vehicle 14 of particular focus has specialized duty equipment 22 which makes it suitable for the performance of professional functions associated with different fields, amongst which are the medical industry, law enforcement, firefighting, the veterinary industry, the human and property rescue industry, etc.

For example, the mobile vehicle 14 may be used to assist a veterinary function as by incorporating equipment 22 in the form of cages, grooming equipment, mobile medical treatment of pets, etc.

The specialized equipment 22 may be that used on mobile vehicles 14 in law enforcement, such as electronic components that require a touch input from the operator. These may be related to data retrieval, radar speed detection, etc. Additionally, police vehicles commonly include safety dividers and restraint devices and equipment.

A further vehicle focus relates to those involved with emergency medical services. Ambulances, mobile medical units, etc., commonly have equipment allowing them to function as mobile hospital and emergency rooms, including a host of conventional electronic medical monitoring and treatment devices, portable instruments, gurneys, wheelchairs, etc., all of which commonly are repeatedly handled by patients and medical personnel throughout events and procedures.

The same types of equipment are commonly present in firefighting vehicles, which are used not only on sites where fires have started but also to assist victims of many types of accidents, including those involving other vehicles.

Common to these commercial vehicles is the movement of many different persons into and out of the inside volume 12 while bringing foreign articles therein as well as contacting basic equipment and structures that bound the inside volume 12 and are built-in or reside separably therewith in.

As noted in the Background section herein, these commercial vehicles present a particular risk to the occupants thereof since they are used in performing many activities related to persons with conditions that make them high risk candidates for transmission of dangerous microorganisms to surfaces and into the air. At the same time, these vehicles are commonly in active use without any significant downtime, which makes disinfecting difficult to schedule. For example, police cars may be handed off from one shift to the next such that there may be no downtime for days. Over an extended time period, multiple police personnel may enter the internal volume and touch surfaces therewithin. At the same time, persons with unknown conditions and backgrounds may be introduced to the inside volume and may introduce a wide range of germs to the inside volume.

Figure 5:
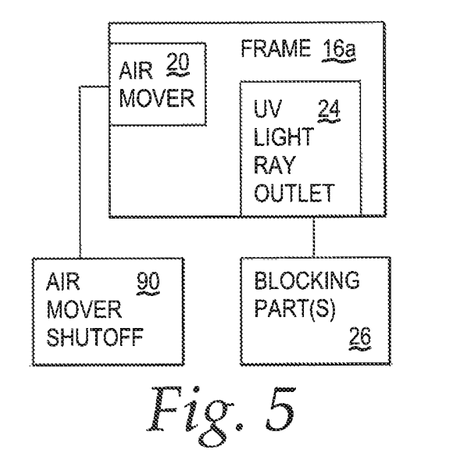
FIG. 5 is a schematic representation of a version of a frame that is part of the treatment unit in FIGS. 1-3.

In one preferred form, as shown in FIG. 5, a frame 16a for the inventive treatment unit has an associated outlet 24 for UV light rays generated by the UV light source 18. At least one blocking part 26 is movable relative to the frame 16a to have different relationships with the outlet 24. With the treatment unit having the frame 16a, the treatment unit is changeable between: a) a first state wherein the blocking part 26 is in a relationship to the outlet 24 so that a predetermined part of the inside volume is strategically blocked from direct exposure to UV light rays generated by the UV light source 18; and b) a second state wherein the blocking part(s) 26 has a second relationship to the outlet 24 such that at least a portion of the predetermined part of the inside volume is directly exposed to UV light rays from the UV light source 18.

By making different constructions for the blocking part(s) 26 and UV light ray outlet 24, the relationship therebetween can be changed, preferably between functioning as primarily an air treatment unit and primarily a surface treatment unit with incidental air treatment. Of course, the frame 16a might be movable relative to the part(s) 26 and thus in the description and claims herein, these reversible designs are considered to be the same.

As one example, with the treatment unit in the first state, substantially the entire inside volume 12 may be protected from direct exposure to the UV light rays. In the second state, substantially the entire inside volume 12 may be directly exposed to UV rays to have concentrated surface treatment. Variations between these extremes may be arrived at. For example, in the first state, the UV rays may be strategically blocked as to avoid direct contact with a driver of the vehicle, while allowing certain direct transmission to surfaces for disinfecting thereof.

Figure 6:
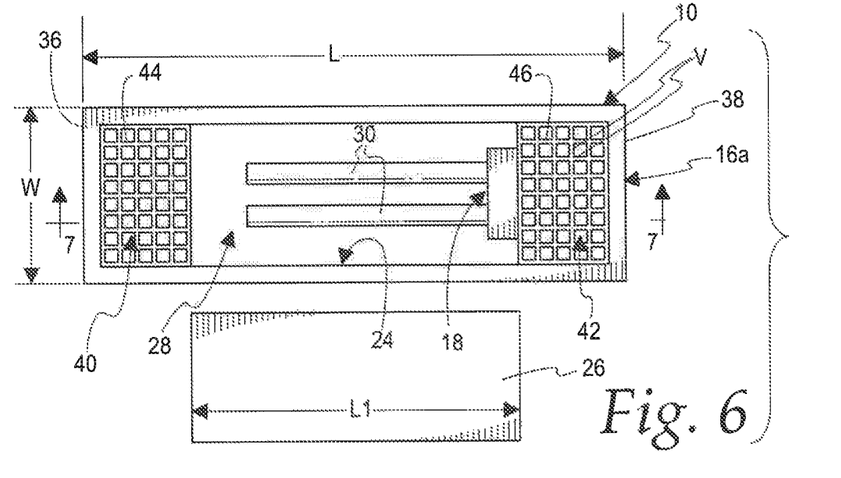
FIG. 6 is an exploded bottom view of one exemplary form of treatment unit as shown in FIGS. 1, 2, and 5.
Figure 7:
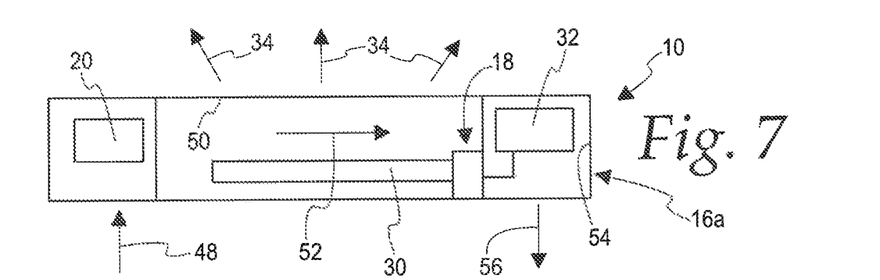
FIG. 7 is a sectional view of the treatment unit taken along line 7-7 of FIG. 6.

In FIGS. 6 and 7, one exemplary form of the treatment unit 10 is shown with the frame 16a. The exemplary frame 16a has a generally rectangular shape with a length L and width W. The rectangular shape is not a requirement.

The treatment unit 10 may be mounted from a ceiling, a floor, a vertical wall, or elsewhere. The exemplary, but not limiting, mounting location herein is on a ceiling and thus the top and bottom identifications apply to this particular operative position but are arbitrary designations.

The treatment unit may be powered off of the mobile vehicle power source or may be independently powered, as by a battery and/or off of a conventional electrical supply—120 volt or other capacity.

The frame 16a bounds a flow control space/sub-volume 28 within which the UV light source 18 is mounted. The UV light source 18, as depicted, consists of two UV light generating bulbs 30 that are cantilever mounted and have lengths substantially aligned with the length of the frame 16a. A ballast/converter 32 is also shown mounted within the space 28.

With the light source 18 operated, UV rays project outwardly from the bulbs 30, as indicated by the arrows 34 through an outlet 24. Thus, the UV rays disinfect surfaces in a line of sight with the bulbs 30.

The aforementioned blocking part 26, shown as a flat plate, fits to the frame 16a and underlies and covers the bulbs 30 to substantially fully block transmission of rays from the bulb 30 downwardly from the space 28. In this embodiment, the plate 26 fully blocks the open frame region/outlet 24. However, this is not a requirement, as strategic blocking may be arrived at to combine air treatment with some surface treatment. The plate 26 may be press fit and frictionally held in place and/or held in place on the frame 16a by fasteners.

The length L1 of the part 26 is less than the length L so that regions of the space 28 at the opposite ends 36, 38 of the space 28 remain uncovered by the plate 26. The uncovered region at the end 36 defines an air inlet at 40 with a corresponding region at the opposite end 38 defining an air outlet 42. Separate grills 44, 46, matched respectively to the dimensions of the air inlet 40 and air outlet 42, allow air passage therethrough. The exemplary grill 46 may have guide surfaces/vanes V, which disperse disinfected air to within the inside volume 12.

An air mover/fan 20 draws air within the surrounding space through the inlet 40 in the direction of the arrow 48. The incoming flow pattern is redirected by a downwardly facing frame surface 50 lengthwise in the direction of the arrow 52 and continues to where it is intercepted by a frame surface 54, substantially orthogonal to the frame surface 50, which causes the air to redirect and expel from the outlet 42 in the direction of the arrow 56 through the grill 46.

Accordingly, the environmental air is caused to move in a flow path lengthwise of the frame 16a and substantially parallel to the length of the bulbs 30 to be treated by UV rays generated thereby. The disinfected air is thus discharged from the outlet generally in the direction of the arrow 56 but is caused to disperse through the grill 46 to expand into the space. The treatment unit 10 thus creates a circulating flow pattern within the air volume within which it resides.

With the part 26 in place on the frame 16a, the treatment unit is in the aforementioned first state wherein a predetermined part of the inside volume 14 is strategically blocked by the part 26. With the part 26 removed, the treatment unit is in the aforementioned second state wherein at least a portion of the predetermined part of the inside volume is directly exposed to UV light rays from the UV light source.

Figure 8:
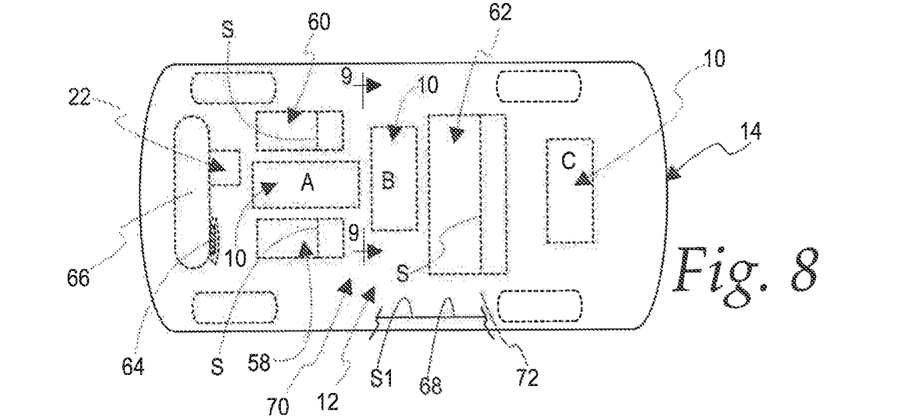
FIG. 8 is a plan view of a mobile vehicle partially broken away and with the inventive treatment unit in different operative positions thereon.
Figure 9:
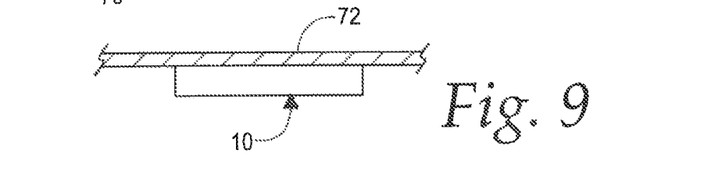
FIG. 9 is a cross-sectional view of the vehicle taken along the line 9-9 of FIG. 8 and showing the inventive treatment unit in an operative position at one location thereon.

In one exemplary application, as shown in FIGS. 8 and 9, the mobile vehicle 14 is a car, van, SUV, or the like with the inside volume 12 containing a driver's seat 58, a front passenger seat 60, and an elongate rear passenger seat 62. The driver's seat 58 is in proximity to a steering wheel 64. In a police-type vehicle, equipment 22 typically might include a built-in or mobile computer, speed detection equipment, etc., which occupants of one or both of the seats 58, 60 may operate from a sitting position, commonly by providing inputs through a touchpad. Equipment 22 is either in the vicinity of, or part of, a conventional-type dashboard 66.

The inside volume 12 is bounded by a peripheral wall surface 68, a floor 70, and a roof/ceiling 72.

The treatment unit 10 can be provided in any number and placed in an operative position at any location within the vehicle 14. As but examples, three alternative locations for the treatment unit 10 are indicated at A, B, and C, with these locations being representative in nature only.

At the location A, the length of the treatment unit 10 is aligned with the length of the vehicle 14 between the seats 60, 62.

At the B location, the length of the treatment unit 10 extends side-to-side between the seats 58, 60 and the seat 62.

At the C location, the treatment unit 10 is over what is used as an open cargo space. The alignment is generally the same as at location B.

The treatment unit 10 is maintained in its operative position at locations A, B, and C by mounting the frame to the roof/ceiling 72.

As noted above, the treatment unit 10 can be constructed so that with the treatment unit in the operative position and placed in the first state, direct exposure to generated UV rays can be strategically controlled. In this case, using the treatment unit at the A location, in the first state, preferably there will be no direct exposure to UV light of a driver in the seat 58 or a passenger in either of the seats 60, 62. Thus, it is contemplated that the vehicle 14 can be safely driven with passengers without direct exposure to UV light generated by the light source 18 while operating the treatment unit in its first state.

By changing the treatment unit 10 at the A location from the first state into the second state, UV light rays generated may be directed against at least part of at least one of, and preferably all of, the dashboard 66, the steering wheel 64, seat surfaces S against which occupants can bear to be maintained in a sitting position, and a surface S1 of the peripheral wall 68.

Figure 10:
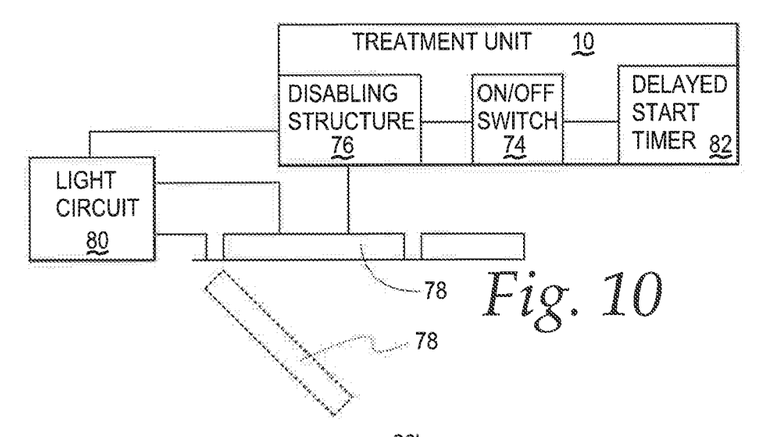
FIG. 10 is a schematic representation of a modified form of treatment unit with a disabling structure operable through an access door on a movable vehicle.

As shown in FIG. 10, the treatment unit 10 may have an on/off switch 74 and incorporate a disabling structure 76. The disabling structure 76, upon being actuated, changes the treatment unit from an "on" state to an "off" state by controlling the switch 74. Alternatively, the actuated disabling structure may change the treatment unit 10 from the second state into the first state.

Further, the switch 74 may be directly controlled by manipulating components, from within or outside of the vehicle 14, or may be Bluetooth operated, as by a cell phone.

The disabling structure 76 is actuated in response to an entry door 78 on the vehicle 14 moving from a closed position, as shown schematically in FIG. 10, into an open position, shown in dotted lines in that same Figure. The disabling feature performs at least with the treatment unit in the second state wherein a person entering the inside volume 12 could be exposed directly to UV rays.

The disabling structure 76 may be directly connected, mechanically and/or electrically, to the door 78 or may be electrically connected, as to a light circuit 80, that is responsible for causing internal lights to be illuminated as an incident of the door 78 being opened.

The disabling structure may have an associated motion sensor that causes the treatment unit 10 to be changed to the "off" state as upon detecting a person entering, or moving within, the inside volume 12 with the treatment unit 10 in the second state. Alternatively, the motion sensor might cause the treatment unit 10 to change from the second state into the first state upon being activated.

The disabling structure 76 may be designed so that the passenger is allowed to open the entry door 78 without turning the treatment unit off with the treatment unit in the first state, wherein there is no danger of direct exposure of the entering person to UV light rays.

As a convenience to the operator, the treatment unit 10 in FIG. 10 may further be provided with a delayed start timer 82. The delayed start timer 82 may be activated so that changing of the treatment unit from the "off" state into the "on" state is delayed by a set or selected time interval, which may be on the order of one minute or longer. This allows an individual to actuate the delayed start timer 82 from within the vehicle with the treatment unit 10 in the second state and to exit the inside volume before the treatment unit 10 changes into the "on" state wherein the UV rays might be generated directly towards the person. The delayed start timer 82 may be operated by a switch from within or outside the vehicle 14, which may involve manual movement of a component or operation using Bluetooth technology, as from a cell phone.

The delayed start timer 82, or another component, may cause the treatment unit 10 to shut off after a fixed or settable time interval and may include a counter for operating time and UV usage.

The generic depictions of the invention herein are intended to encompass the specific forms of the invention described herein and virtually a limitless number of variations of the individual components and their interaction. The specific examples herein are not to be viewed as limiting.

Figure 11:
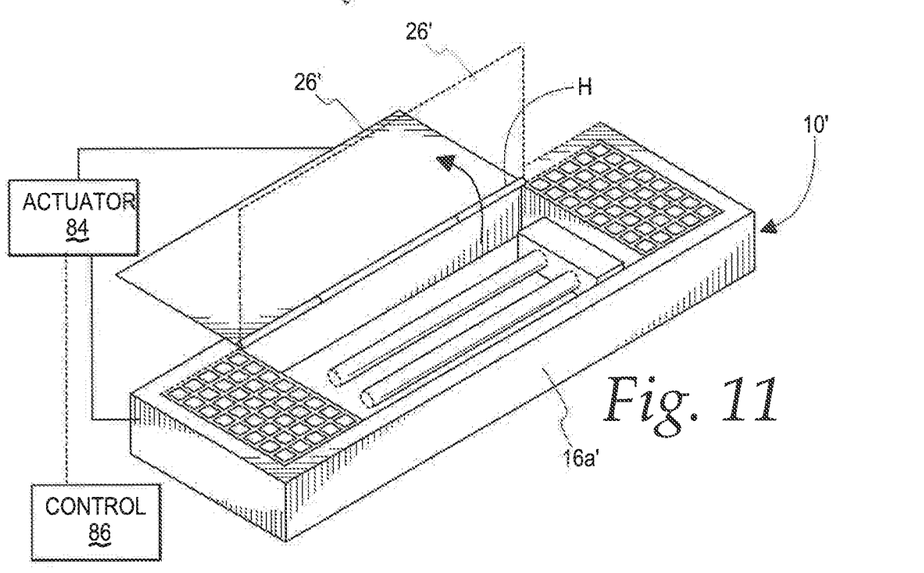
FIG. 11 is a perspective view of a modified form of treatment unit as shown in FIGS. 1, 2, and 5.

As one example, as shown in FIG. 11, a modified form of part 26', corresponding to the part 26 described above, is incorporated into the frame 16a' through a hinge arrangement H which allows pivoting from a fully covering position, corresponding to the first state for the treatment unit 10', to the solid line position, corresponding to the second state for the treatment unit 10'. The part 26' may be maintained at an intermediate position, as indicated in dotted lines, while the treatment unit 10' is operated.

The parts 26, 26' may be manually repositioned or positioned as in FIG. 11 through an actuator 84. The actuator 84 may be operated through a control 86, either on the actuator 84, as indicated by the dotted lines in FIG. 11, or from a remote location spaced from the actuator 84 either on or apart from the vehicle 14. As one example, the actuator 84 may be Bluetooth operated, as through a cell phone.

Figure 12:
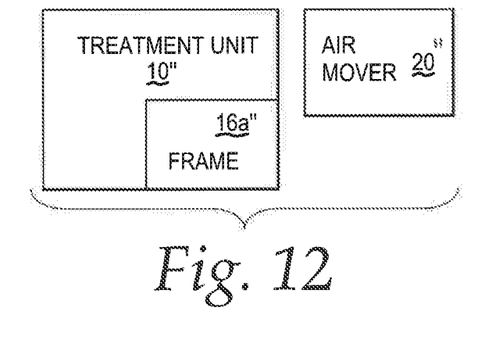
FIG. 12 is a schematic representation of a further modified form of the inventive treatment unit.

In another variation as shown in FIG. 12, a treatment unit 10" has a frame 16a" similar to the frames 16a, 16a', with the exception that the air mover 20" is standard equipment built into the particular vehicle to which the treatment unit 10" is operatively mounted. The treatment unit 10" can be strategically placed with respect to a vent or a predetermined air flow pattern from the vehicles normal heating or air conditioning unit. Flow routing structure associated with an air inlet may be utilized for better efficiency. The treatment unit 10" can otherwise be made to operate substantially as the aforementioned treatment units 10, 10'.

With the inventive treatment unit operatively installed in a vehicle, substantial flexibility is afforded regarding disinfecting air and surfaces within the inside vehicle volume 12. For example, when the vehicle is not occupied, the treatment unit can be placed in the second state to effect primarily surface treatment and incidental air treatment. By entering the vehicle, the treatment unit is preferably turned off, whereupon the treatment unit can be changed into the first state which allows ongoing disinfecting of the air within the inside volume 12 while the vehicle is occupied and potentially driven with any number of passengers. Thus, potentially ongoing disinfecting can occur, which is particularly desirable when a vehicle is in constant use potentially for over extended periods.

As shown in FIG. 5, an optional shutoff 90 can be provided to change the air mover 20 from an "on" state into an "off" state as an incident of the treatment unit 10 being changed from the first state into the second state.

One or more treatment units can be strategically placed to generate the most efficient circulation of air through the treatment unit in the first state and to allow all critical surfaces to be exposed directly to UV light with the treatment unit in the second state. The part(s) 26 can be strategically designed to allow controlled surface treatment, if desired, with the treatment unit in the first state.

While the focus above is on protecting human occupants, this category is intended to encompass animals that could also be injured by direct exposure to UV light rays.

All system functions described may be controlled through Bluetooth operation, as by using a cell phone, for user convenience.

Additional sanitation may be afforded by using filters, such as HEPA/carbon, to collect particles being drawn towards the air mover 20 and directed away therefrom.

The foregoing disclosure of specific embodiments is intended to be illustrative of the broad concepts comprehended by the invention.

The invention claimed is:

1. A method of treating an inside volume of a mobile vehicle, the method comprising the steps of:
   obtaining a treatment unit placed in an operative position with respect to the mobile vehicle, the treatment unit comprising:
   a) a frame;
   b) a source of UV light; and c) an air mover for controllably directing air within the inside volume to be exposed to UV light rays generated by the UV light source, the treatment unit changeable between first and second states;

operating the air treatment unit in the second state wherein surfaces within the inside volume are directly exposed to UV light rays from the source of UV light;

changing the air treatment unit from the second state into the first state by repositioning at least one part of the treatment unit so that the at least one part of the treatment unit strategically blocks UV light rays from the UV light source so that at least part of the surfaces directly exposed to UV light rays from the UV light source with the treatment unit in the second state are not directly exposed to UV light rays from the UV light source; and such that in the first state the frame defines a sub-volume through which air can circulate; and operating the treatment unit in the first state wherein air directed by the air mover is disinfected by UV light rays from the UV light source and distributed within the inside volume.

2. The method of treating an inside volume of a mobile vehicle according to claim 1 wherein the air mover comprises at least one fan.

3. The method of treating an inside volume of a mobile vehicle according to claim 2 wherein with the treatment unit placed in the operative position the frame is mounted to a ceiling on the mobile vehicle.

4. The method of treating an inside volume of a mobile vehicle according to claim 1 wherein the mobile vehicle has at least one seat for an occupant and further comprising the step of operating the treatment unit in the first state with a person situated in the at least one seat so that the person in the at least one seat is not directly exposed to UV light rays from the UV light source.

5. The method of treating an inside volume of a mobile vehicle according to claim 4 wherein the at least one seat is a driver's seat and further comprising the step of operating the treatment unit in the second state with no person situated in the driver's seat so that the driver's seat is directly exposed to UV light rays from the UV light source.

6. The method of treating an inside volume of a mobile vehicle according to claim 5 further comprising the step of operating the treatment unit in the first state with the person in the driver's seat operating the mobile vehicle.

7. The method of treating an inside volume of a mobile vehicle according to claim 4 wherein with the treatment unit in the first state a predetermined part of the inside volume is strategically blocked from direct exposure to UV light rays generated by the UV light source.

8. The method of treating an inside volume of a mobile vehicle according to claim 1 further comprising the step of changing operating the treatment unit in the second state without any person situated in the inside volume.

9. The method of treating an inside volume of a mobile vehicle according to claim 1 wherein the treatment unit has on and off states and comprises a delayed start timer and further comprising the step of activating the delayed start timer to allow a person actuating the delayed start timer from within the inside volume to exit the inside volume before the treatment unit is changed from the off state into the on state with the treatment unit in the second state.

10. The method of treating an inside volume of a mobile vehicle according to claim 1 wherein the mobile vehicle comprises: a) a dashboard; b) a steering wheel; c) seat surfaces against which at least one occupant can be supported in a sitting position; and d) a peripheral wall surface bounding the inside volume, and with the treatment unit in the second state operating the treatment unit causes UV light rays generated by the UV light source to be directed against at least part of at least one of: i) the dashboard; ii) the steering wheel; iii) the seat surfaces; and iv) the peripheral wall surface.

11. The method of treating an inside volume of a mobile vehicle according to claim 10 wherein with the treatment unit in the second state, operation of the treatment unit causes UV light rays generated by the UV light source to be directed against at least part of each of: a) the dashboard; b) the steering wheel; c) the seat surfaces; and d) the peripheral wall surface.

12. The method of treating an inside volume of a mobile vehicle according to claim 1 wherein the mobile vehicle is an emergency vehicle with electronic emergency equipment with operating components exposed within the inside volume.

13. The method of treating an inside volume of a mobile vehicle according to claim 1 wherein the UV light source comprises at least one elongate bulb with a length and the step of operating the treatment unit comprises causing the air mover to move air in a flow path lengthwise of the at least one elongate bulb.

14. The method of treating an inside volume of a mobile vehicle according to claim 1 further comprising the step of changing the treatment unit between the first and second states by manually repositioning the at least one part of the treatment unit.

15. The method of treating an inside volume of a mobile vehicle according to claim 1 wherein the treatment unit comprises an actuator and further comprising the step of causing the actuator to reposition a part of the treatment unit to thereby change the treatment unit between the first and second states.

16. The method of treating an inside volume of a mobile vehicle according to claim 15 further comprising the step of controlling the actuator from a location spaced from the actuator.

17. The method of treating an inside volume of a mobile vehicle according to claim 1 wherein the air mover is mounted on the frame.

18. The method of treating an inside volume of a mobile vehicle according to claim 1 wherein the mobile vehicle has an entry door that has open and closed positions, the treatment unit has on and off states and a disabling structure and further comprising the step of causing the disabling structure to change the treatment unit in the on and second states to be changed into the off state as an incident of the entry door changing from the closed position into the open position.

19. The method of treating an inside volume of a mobile vehicle according to claim 1 wherein the UV rays generated by the UV light source are not capable of penetrating glass.

* * * * *

UNITED STATES PATENT AND TRADEMARK OFFICE
CERTIFICATE OF CORRECTION

| | |
|---|---|
| PATENT NO. | : 10,893,990 B1 |
| APPLICATION NO. | : 16/852277 |
| DATED | : January 19, 2021 |
| INVENTOR(S) | : Mike M. Uda |

It is certified that error appears in the above-identified patent and that said Letters Patent is hereby corrected as shown below:

In the Claims

Column 11 Line 55 Claim 8, should read:
8. The method of treating an inside volume of a mobile vehicle according to claim 1 further comprising the step of operating the treatment unit in the second state without any person situated in the inside volume.

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*